US011925451B2

(12) United States Patent
He et al.

(10) Patent No.: US 11,925,451 B2
(45) Date of Patent: Mar. 12, 2024

(54) METHOD FOR SYNTHESIZING HIGH-QUALITY MAGNETIC RESONANCE IMAGES

(71) Applicant: ZHEJIANG UNIVERSITY, Zhejiang (CN)

(72) Inventors: Hongjian He, Hangzhou (CN); Jun Li, Hangzhou (CN); Xiaozhi Cao, Hangzhou (CN); Qiuping Ding, Hangzhou (CN); Jianhui Zhong, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 813 days.

(21) Appl. No.: 17/035,786

(22) Filed: Sep. 29, 2020

(65) Prior Publication Data

US 2021/0038110 A1 Feb. 11, 2021

Related U.S. Application Data

(63) Continuation of application No. PCT/CN2020/077916, filed on Mar. 5, 2020.

(30) Foreign Application Priority Data

May 14, 2019 (CN) .......................... 201910202207.X

(51) Int. Cl.
  *A61B 5/055* (2006.01)
  *G01R 33/50* (2006.01)
(52) U.S. Cl.
  CPC .............. *A61B 5/055* (2013.01); *G01R 33/50* (2013.01)
(58) Field of Classification Search
  CPC .... A61B 5/055; G01R 33/50; G01R 33/5602; G01R 33/5608
  See application file for complete search history.

(56) References Cited

U.S. PATENT DOCUMENTS

| 6,823,205 B1 | 11/2004 | Jara |
| 2004/0041562 A1 | 3/2004 | Speier |

(Continued)

FOREIGN PATENT DOCUMENTS

| CN | 1618399 A | 5/2005 |
| CN | 101627910 A | 1/2010 |

(Continued)

OTHER PUBLICATIONS

International Search Report (PCT/CN2020/077916); dated: Apr. 29, 2020.

(Continued)

*Primary Examiner* — Hien N Nguyen
(74) *Attorney, Agent, or Firm* — W&G Law Group

(57) ABSTRACT

The present disclosure discloses a method for synthesizing high-quality magnetic resonance images, wherein the method expands the value ranges of echo time TE and repetition time TR in a magnetic resonance signal formula to negative intervals, and expands the contribution of proton density PD to a negative power. The method can effectively reduce the influence of the measurement error of quantitative magnetic resonance imaging tissue parameters on the tissue contrast of the synthetic magnetic resonance image, and can obviously improve the tissue contrast of the synthetic magnetic resonance image. This method will significantly improve the imaging quality of synthetic magnetic resonance imaging, and promote its detection effect in neuroscience and clinical lesions. This method is expected to improve the imaging quality of synthetic magnetic resonance imaging and promote its detection effect in neuroscience and clinical lesions.

1 Claim, 9 Drawing Sheets

(56) References Cited

U.S. PATENT DOCUMENTS

2015/0310650 A1    10/2015   Toshiba et al.
2018/0095152 A1*   4/2018   Triaire .................. A61B 5/055

FOREIGN PATENT DOCUMENTS

| CN | 102749600 A | 10/2012 |
|---|---|---|
| CN | 109938733 A | 6/2019 |

OTHER PUBLICATIONS

Rapid Magnetic Resonance Quantification on the Brain Optimization for Clinical Usage (J.B.M. Warntjes et al.) [Aug. 31, 2008] pp. 320-329.
Synthetic MRI for Clinical Neuroimaging Results of the Magnetic Resonance Image Compilation (MAGiC) Prospective, Multicenter, Multireader Trial (LN.Tanenbaum et al.) [Jun. 30, 2017] pp. 1113-1110.

* cited by examiner

METHOD FOR SYNTHESIZING HIGH-QUALITY MAGNETIC RESONANCE IMAGES

TECHNICAL FIELD

The present disclosure relates to the field of magnetic resonance imaging and image processing, and specifically, to a method for synthesizing high-quality magnetic resonance images.

BACKGROUND

Synthetic magnetic resonance imaging refers to the method of generating various common magnetic resonance images with different contrasts by using a magnetic resonance signal formula after obtaining the quantitative tissue parameters (T1, T2 and PD) of each voxel by quantitative magnetic resonance imaging. Equation (1) represents the signal equation [1] of the Spin Echo (SE) sequence. In formula (1), S represents magnetic resonance signal, PD (Proton Density) represents proton density, T1 represents longitudinal relaxation time, T2 represents transverse relaxation time, TR (Repetition Time) represents repetition time, and TE (Echo Time) represents echo time. PD, T1 and T2 are quantitative magnetic resonance imaging tissue parameters, which can be obtained by quantitative magnetic resonance imaging. TR and TE are scanning parameters of magnetic resonance imaging, and different TR and TE can be set to obtain synthetic magnetic resonance images with different contrasts. In the traditional calculation of synthetic magnetic resonance images, $\beta=1$, TR>TE>0.

$$S \propto PD^{\beta}(1-e^{-TR/T1})e^{-TE/T2} \tag{1}$$

PD, T1 and T2 of each voxel can be obtained by quantitative magnetic resonance imaging. For example, the T1 value can be obtained by an Inversion Recovery (IR) sequence with multiple inversion times (TI). The signal intensities of multiple TI values are fitted, and the T1 value of each voxel in the imaging area is calculated. The T2 value can be calculated by signal fitting of the SE sequence with multiple echoes. The novel quantitative magnetic resonance sequence can simultaneously obtain PD, T1 and T2 of each voxel in one scan, including QRAPMASTER (Quantification of Relaxation Times and Proton Density by Multiecho acquisition of a saturation-recovery using Turbo spin-Echo Readout) [2], MDME(Multiple Dynamic Multiple Echo) [3] and MRF (Magnetic Resonance Fingerprinting) [4] etc.

The development of quantitative magnetic resonance sequences also promotes the development of synthetic magnetic resonance imaging. There has been extensive research on synthetic magnetic resonance imaging, and the image quality of synthetic magnetic resonance images has been recognized by researchers. In the calculation of the synthetic magnetic resonance image, when scanning parameters such as TR and TE are set to be the same as those of conventional scanning, the image quality of the synthetic magnetic resonance image is close to that of the conventional scanning. Synthetic magnetic resonance images can also be used in the diagnosis of diseases. In some diseases, the diagnostic quality is similar to that of conventional magnetic resonance images [5]. Synthetic magnetic resonance images can also be found in clinical disease detection applications for children [6]. At present, the main focus of research and application is to get a variety of synthetic magnetic resonance images with different contrasts through signal formula fitting, that is, to achieve the purpose of synthesizing magnetic resonance images with various application values by one quantitative scan.

However, synthetic magnetic resonance imaging still has some obvious limitations. Among them, the contrast of the tissue or lesion to be detected and the accuracy of its contrast are the main points. For example, the common synthetic T2-FLAIR images cannot achieve the complete CSF inhibitory effect [3]. The main reason is that in the calculation of the existing synthetic magnetic resonance imaging method, the scanning parameters such as TR and TE are set to be the same or similar to those of the conventional scanning, so that the image contrast of the synthetic magnetic resonance image can be the same or similar to that of conventional scanning. In this scenario, the synthetic magnetic resonance image can only achieve the effect similar to that obtained by conventional scanning. In addition, there are errors in the measurement of quantitative magnetic resonance imaging tissue parameters. If the difference of quantitative parameters of different tissues cannot be significantly larger than the measurement error, the accuracy of synthetic magnetic resonance images will be questioned. Therefore, the contrast and accuracy of existing synthetic magnetic resonance images are not significantly better than those of conventional clinical scanning images, which greatly limits the further practical application of this technology in clinic.

[1] Bernstein M, King K, Zhou K. Handbook of MRI Pulse Sequences. Elsevier Science, 2004. ISBN: 9780080533124.

[2] Warntjes J B M, Leinhard O D, West J, Lundberg P. Rapid magnetic resonance quantification on the brain: optimization for clinical usage. Magn Reson Med, 2008;60:320-329.

[3] Tanenbaum L N, Tsiouris A J, Johnson A N, Naidich T P, DeLano M C, Melhem E R. Quarterman P, Parameswaran S X., Shankaranarayanan A, Goyen M, A S. Synthetic MRI for clinical neuroimaging: results of the Magnetic Resonance Image Compilation (MAGiC) prospective, multicenter, multireader trial. AJNR Am J Neuroradil, 2017;38: 1103-10

[4] Ma D, Gulani V, Seiberlich N, Liu K, Sunshine J L, Duerk J L, Griswold M A. Magnetic resonance fingerprinting. Nature, 2013;495: 187-192.

[5] Blystad I, Warntjes J B, Smedby O, Landtblom A M, Lundberg P, Larsson E M. Synthetic MRI of the brain in a clinical setting. Acta Radiol, 2012;53:1158-1163.

[6] Betts A M, Leach J L,Jones B V, Bin Zhang, Suraj Serai. Brain imaging with synthetic MR in children: clinical quality assessment. Neuroradiology, 2016; 58:1017-1026.

SUMMARY

In order to improve the tissue contrast of synthetic magnetic resonance imaging and the ability to resist measurement errors, the present disclosure provides a method for synthesizing high-quality magnetic resonance images, which expands the value ranges of echo time TE and repetition time TR in a magnetic resonance signal formula to negative intervals, and expands the contribution of proton density PD to a negative power. The method can effectively reduce the influence of the measurement error of quantitative magnetic resonance imaging tissue parameters on the tissue contrast of the synthetic magnetic resonance image, and can obviously improve the tissue contrast of the synthetic magnetic resonance image. This method will significantly improve the imaging quality of synthetic magnetic resonance imaging, and promote its detection effect in neuroscience and clinical lesions.

The technical solution adopted by the present disclosure is a method for synthesizing high-quality magnetic resonance images, comprising the steps of:

(1) scanning a subject by a magnetic resonance scanner, and obtaining proton density PD, longitudinal relaxation time T1 and transverse relaxation time T2 by further reconstruction; and (2) substituting PD, T1 and T2 obtained in the step (1) into formula (1) to obtain the magnetic resonance signal S:

$$S \propto PD^{\beta}(1-e^{-TR/T1})e^{-TE/T2} \tag{1}$$

where $\beta$ is negative; TR represents simulated repetition time and is negative; and TE represents simulated echo time and is negative.

Compared with the background art, the method has the beneficial effects that the value ranges of TE and TR are expanded to negative intervals, and the contribution of PD is expanded to negative power, so that the influence of measurement errors of quantitative magnetic resonance imaging tissue parameters on the tissue contrast of synthetic magnetic resonance images can be effectively reduced, the tissue contrast of synthetic magnetic resonance images can be significantly improved, and unexpected technical effects are achieved. On the basis of not affecting the original advantages of synthetic magnetic resonance imaging, this method further significantly improves the image quality of synthetic magnetic resonance imaging and promotes its practical popularization and application in neuroscience and clinical imaging detection.

BRIEF DESCRIPTION OF DRAWINGS

In order to explain the technical solution of the present disclosure more clearly, the drawings needed to be used in the embodiment description will be briefly introduced below. Obviously, the drawings in the following description are only specific embodiments described in this application, and are not a limitation on the protection scope of the present disclosure. For those skilled in the art, on the premise of not paying creative labor, of course, some other embodiments and drawings can be obtained according to the following embodiments and drawings of the present disclosure.

DESCRIPTION OF EMBODIMENTS

In order to make a person skilled in the art better understand the technical solution in this application, the present disclosure will be further explained with reference to the attached drawings. The calculation of synthetic magnetic resonance images of the SE sequence is taken as an example. However, this is only a part of the embodiments of this application, but not all of them. Based on the specific embodiments described in this application, other embodiments obtained by other people in the field without creative work should fall within the conceptual scope of the present disclosure.

Preferred embodiments of the present disclosure are described below with reference to the accompanying drawings.

Generally speaking, in the calculation of the synthetic magnetic resonance image, the value ranges of TE and TR are expanded to negative intervals, and the contribution of PD is expanded to a negative power, thereby improving the contrast between various tissues in the synthetic magnetic resonance image and the contrast between diseased tissues and normal tissues with increased PD, T1 and T2.

In the calculation of a synthetic magnetic resonance signal, according to the magnetic resonance signal formula, when TR is negative, the obtained signal intensity is negative. Therefore, when TR is negative, its signal intensity is the absolute value of the signal intensity calculated by using the magnetic resonance signal formula.

Figure 1:
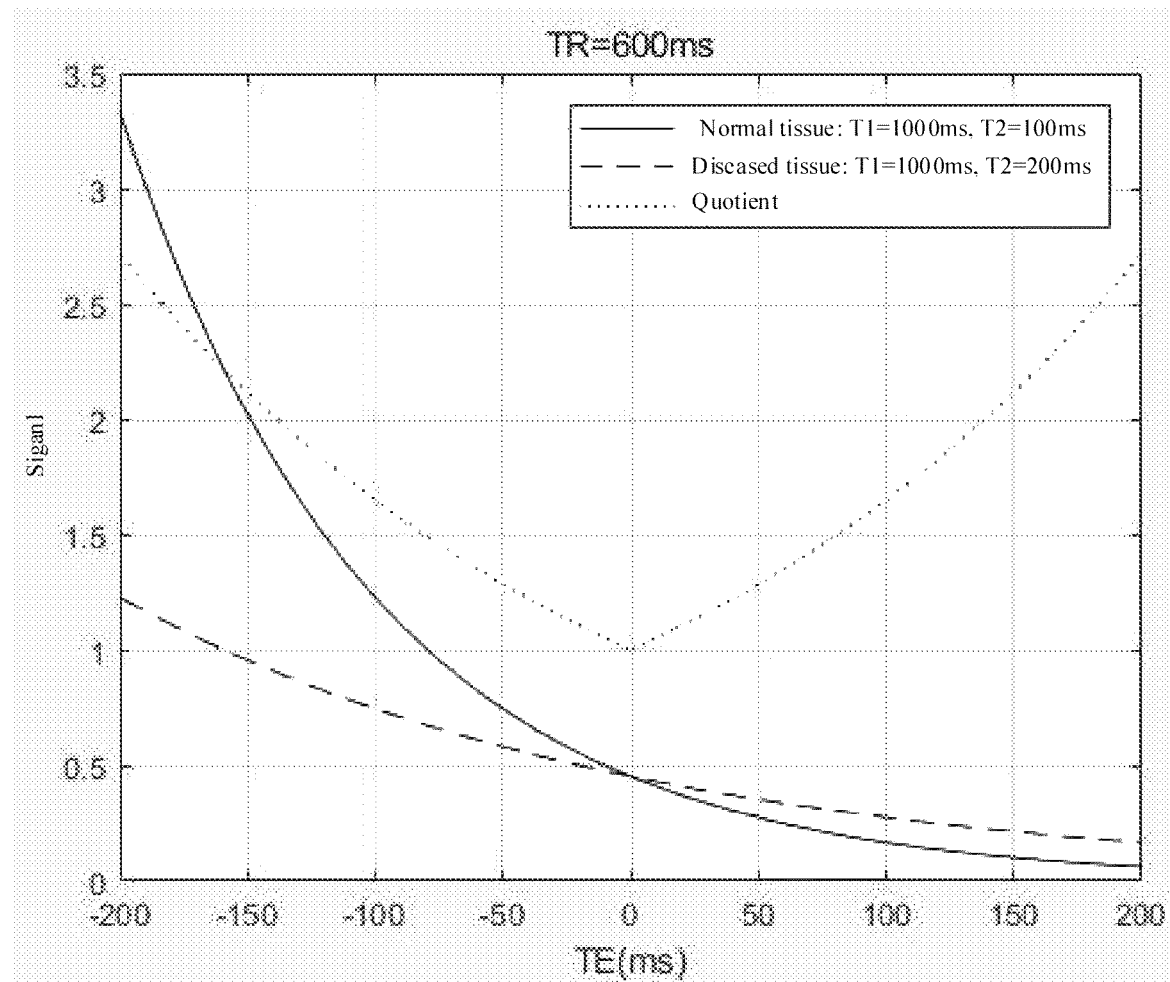
FIG. 1 is a simulation of the change of signal intensities of two tissues with different T2 in the SE sequence when TR is 600 ms, and the change of a quotient of a larger tissue signal intensity divided by a smaller tissue signal intensity with TE.

As shown in FIG. 1, when other conditions are the same, using the signal formula of the SE sequence, the influence of TE on the signals of two tissues with only T2 difference and the influence of TE on the quotient of the signals of the two tissues are simulated when TR is 600 ms. It is assumed that the tissue with a smaller T2 is a normal tissue and the tissue with a larger T2 is a diseased tissue. When TE is positive, the signal of a pathological tissue with a larger T2 value is higher, while the signal of the normal tissue with a smaller T2 value is lower. When TE is negative, the signal of the pathological tissue with a larger T2 value is lower, and the signal of the normal tissue with a smaller T2 value is higher. When the absolute value of TE is the same, the quotient of the larger tissue signal intensity divided by the smaller tissue signal intensity is equal, and the larger the absolute value of TE, the greater the quotient.

Figure 2:
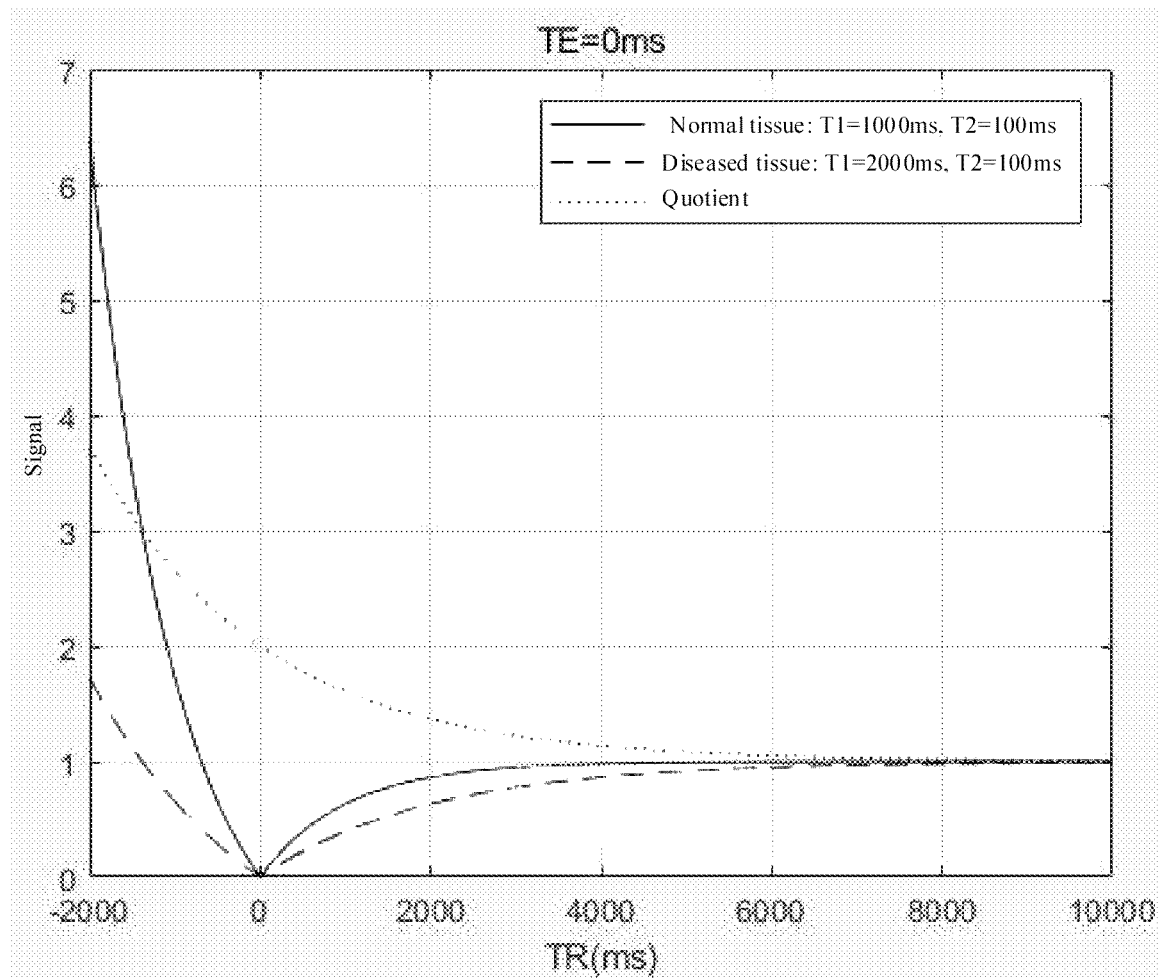
FIG. 2 is a simulation of the change of absolute values of signals of two tissues with different T1 in the SE sequence when TE is 0 ms, and the change of a quotient of the absolute value of a larger tissue signal divided by the absolute value of a smaller tissue signal with TR.

As shown in FIG. 2, when other conditions are the same, using the signal formula of the SE sequence, the influence of TR on the signals of two tissues with only T1 difference and the influence of TR on the quotient value of the signals of the two tissues are simulated when TE is 0 ms. It is assumed that the tissue with a smaller T1 is a normal tissue and the tissues with a larger T1 is a diseased tissue. No matter whether TR is positive or negative, the signal of the normal tissue with a smaller T1 is larger than that of the diseased tissue with a larger T1. When TR is negative, the quotient of the normal tissue signal divided by the pathological tissue signal is larger, and the larger the absolute value of TR is, the larger the quotient of the normal tissue signal divided by the pathological tissue signal is.

Figure 3:
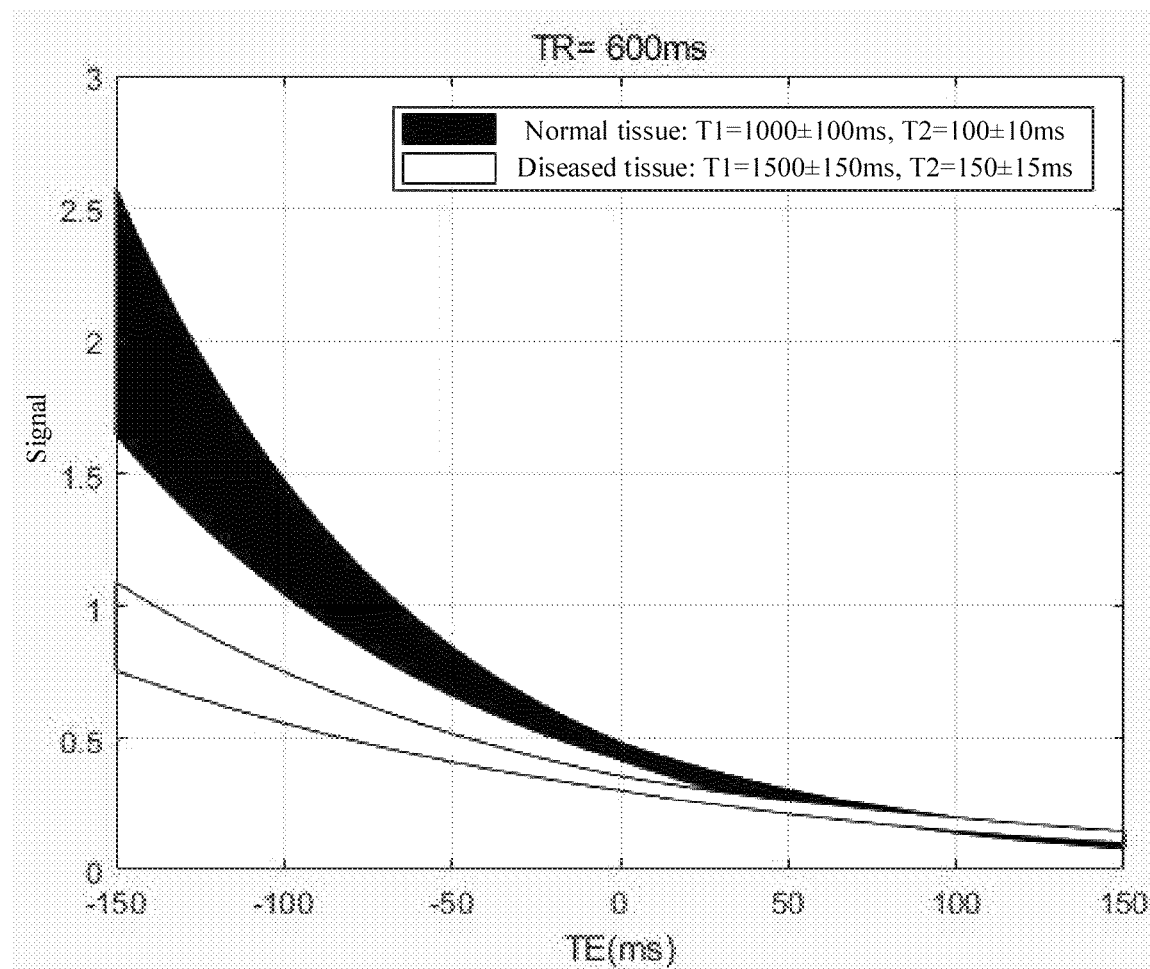
FIG. 3 is a simulation of the change of signal intensities of two kinds of tissues with TE in the SE sequence when TR is 600 ms, and T1 and T2 are different and fluctuate in a certain range for the two tissues.

As shown in FIG. 3, when other conditions are the same, the signal formula of the SE sequence is used to simulate the influence of TE on the signals of two tissues with different T1 and T2 and with T1 and T2 fluctuating within a certain range when TR is 600 ms. When TE is a positive number, the signals of the two tissues may overlap. When TE is negative, the signals of two tissues will not overlap, and with the increase of absolute value of TE, the difference between the signals of two tissues becomes larger and larger.

Figure 4:
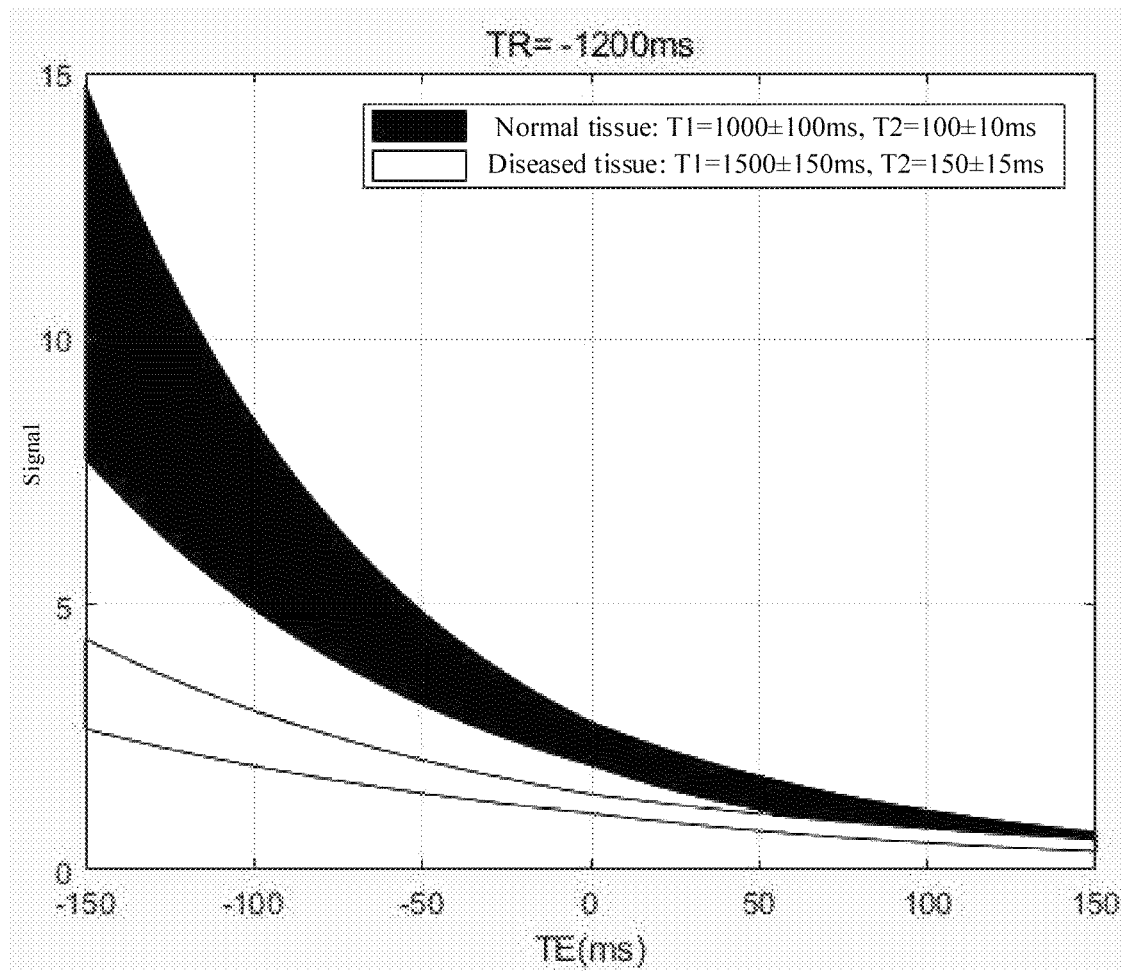
FIG. 4 is a simulation of the change of absolute values of signals of two tissues with TE in the SE sequence when TR is −1200 ms, and T1 and T2 are different and fluctuate in a certain range for the two tissues.

As shown in FIG. 4, when other conditions are the same, the influence of TE on the signals of two tissues with different T1 and T2 and with T1 and T2 fluctuating within a certain range when TR is −1200 ms is simulated using the signal formula of the SE sequence. When TE is a positive number, the signals of the two tissues may overlap. When TE is negative, the signals of two tissues will not overlap, and with the increase of absolute value of TE, the difference between the signals of two tissues becomes larger and larger.

Comparing FIG. 3 with FIG. 4, TR in FIG. 3 is 600 ms, and TR in FIG. 4 is −1200 ms. By comparing FIG. 3 with FIG. 4, it can be seen that when TE is less than 0, the difference between the two tissue signals in FIG. 4 is larger than that in FIG. 3 under the same TE. Therefore, when TE and TR are negative, the contrast between different tissues can be increased, and when there is a measurement error in quantitative magnetic resonance imaging tissue parameters, setting TE and TR as negative can effectively reduce the influence of the measurement error in quantitative magnetic resonance imaging tissue parameters on tissue contrast of synthetic images.

There is a positive correlation between T1 and T2 in most brain tissues, and with the increase of free water in many pathological tissues, the values of T1 and T2 will also increase. It can be seen from FIG. 1 that when TE is negative, the larger T2 is, the lower the signal is. It can be seen from FIG. 2 that regardless of whether TR is positive or negative, the larger T1 is, the lower the tissue signal is. Therefore, when TE and TR are set to be negative, the signals of tissues with larger T1 and T2 are lower, thus improving the contrast between different tissues in the synthetic magnetic resonance image, and the contrast of the synthetic magnetic resonance image obtained is higher than that of the synthetic magnetic resonance image obtained when TR is positive. Therefore, setting TE and TR as negative numbers can improve the contrast between different tissues in synthetic magnetic resonance images, and also improve the contrast between normal tissues and diseased tissues with elevated T1 and T2.

Figure 6:
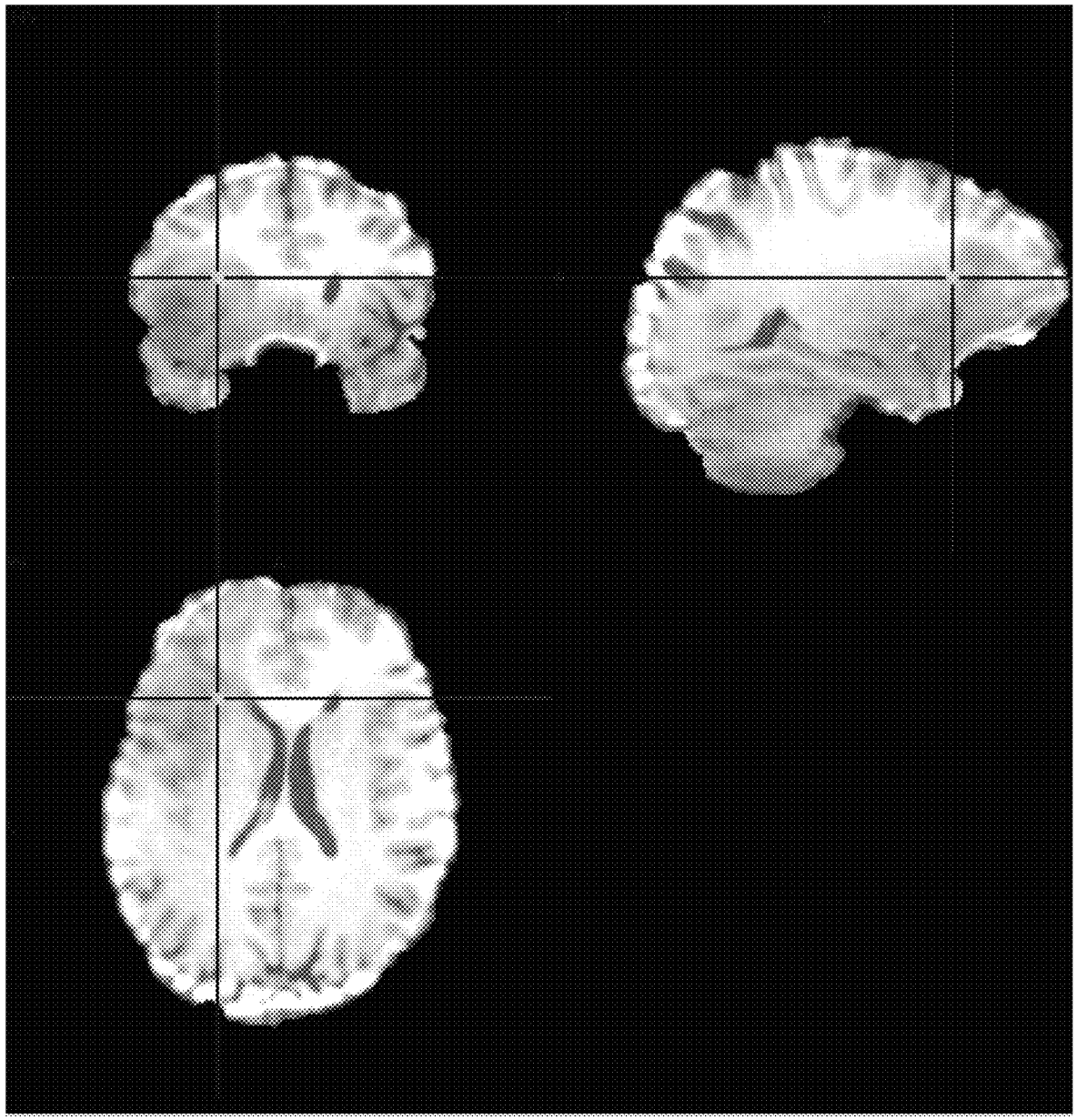
FIG. 6 is a synthetic magnetic resonance image obtained by using PD, T1 and T2 obtained by quantitative magnetic resonance imaging, by using the signal formula of the SE sequence, setting TR to 600 ms and TE to 6 ms, taking the positive $1^{st}$ power of PD and taking the absolute value of the signal.

As shown in FIG. 6, by using PD, T1, T2 obtained by quantitative magnetic resonance imaging, using the signal formula of the SE sequence, setting TE as 6 ms, TR as 600 ms, and taking the positive $1^{st}$ power of PD, a synthetic magnetic resonance image is obtained through calculation.

Figure 7:
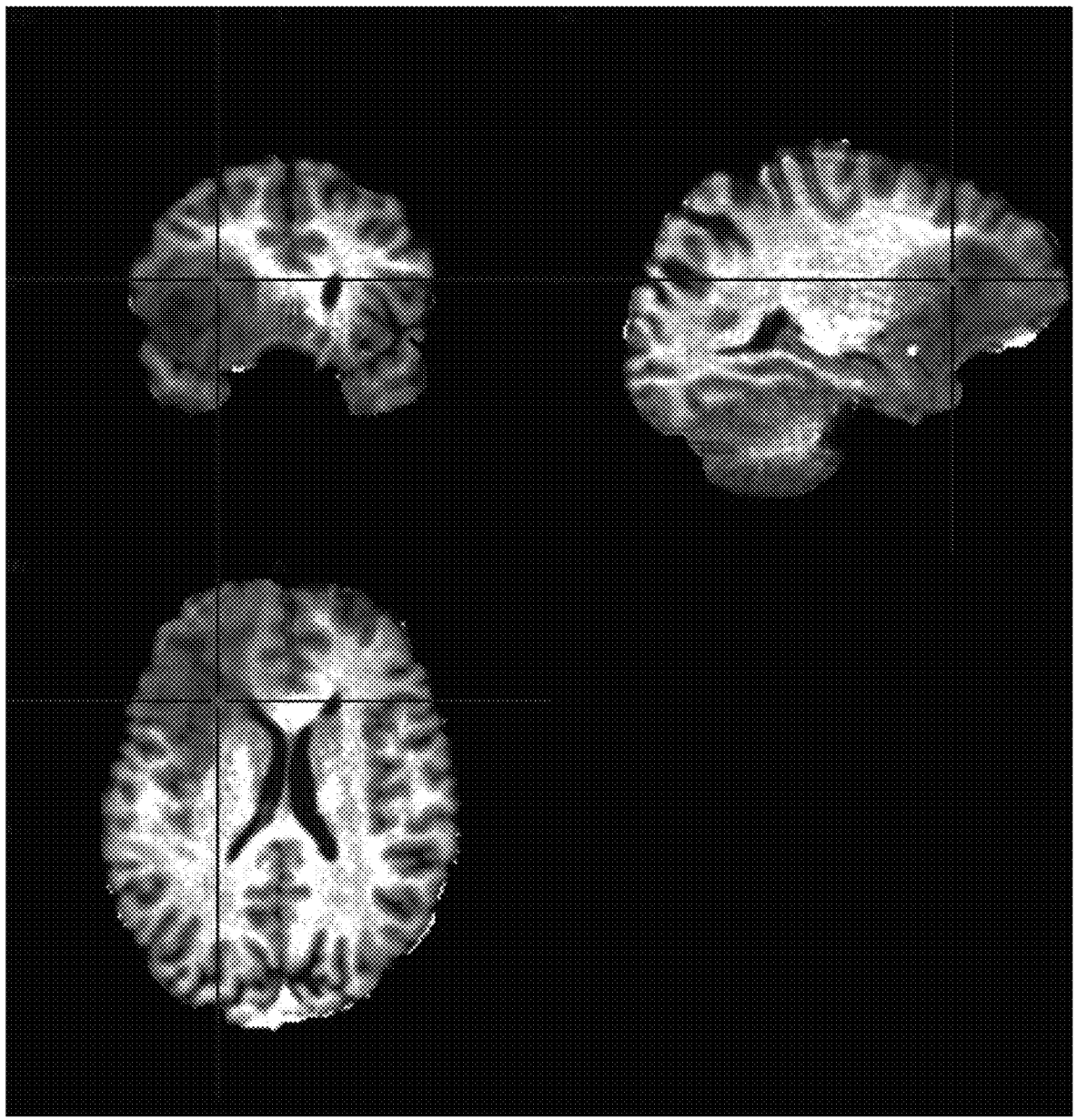
FIG. 7 is a synthetic magnetic resonance image obtained by using PD, T1 and T2 obtained by quantitative magnetic resonance imaging, by using the signal formula of the SE sequence, setting TR to −1200 ms and TE to −50 ms, taking the positive $1^{st}$ power of PD and taking the absolute value of the signal.

As shown in FIG. 7, by using PD, T1, T2 obtained by quantitative magnetic resonance imaging, using the signal formula of the SE sequence, setting TE as −50 ms, TR as −1200 ms, taking the positive $1^{st}$ power of PD, a synthetic magnetic resonance image is obtained through calculation.

Comparing FIG. 6 with FIG. 7, all conditions are the same except that TE and TR in FIG. 6 are positive numbers, while TE and TR in FIG. 7 are negative numbers. By comparing FIG. 6 with FIG. 7, it can be seen that the contrast of FIG. 7 is greater than that of FIG. 6, so setting TE and TR as negative numbers can effectively improve the contrast of the synthetic magnetic resonance image.

Figure 5:
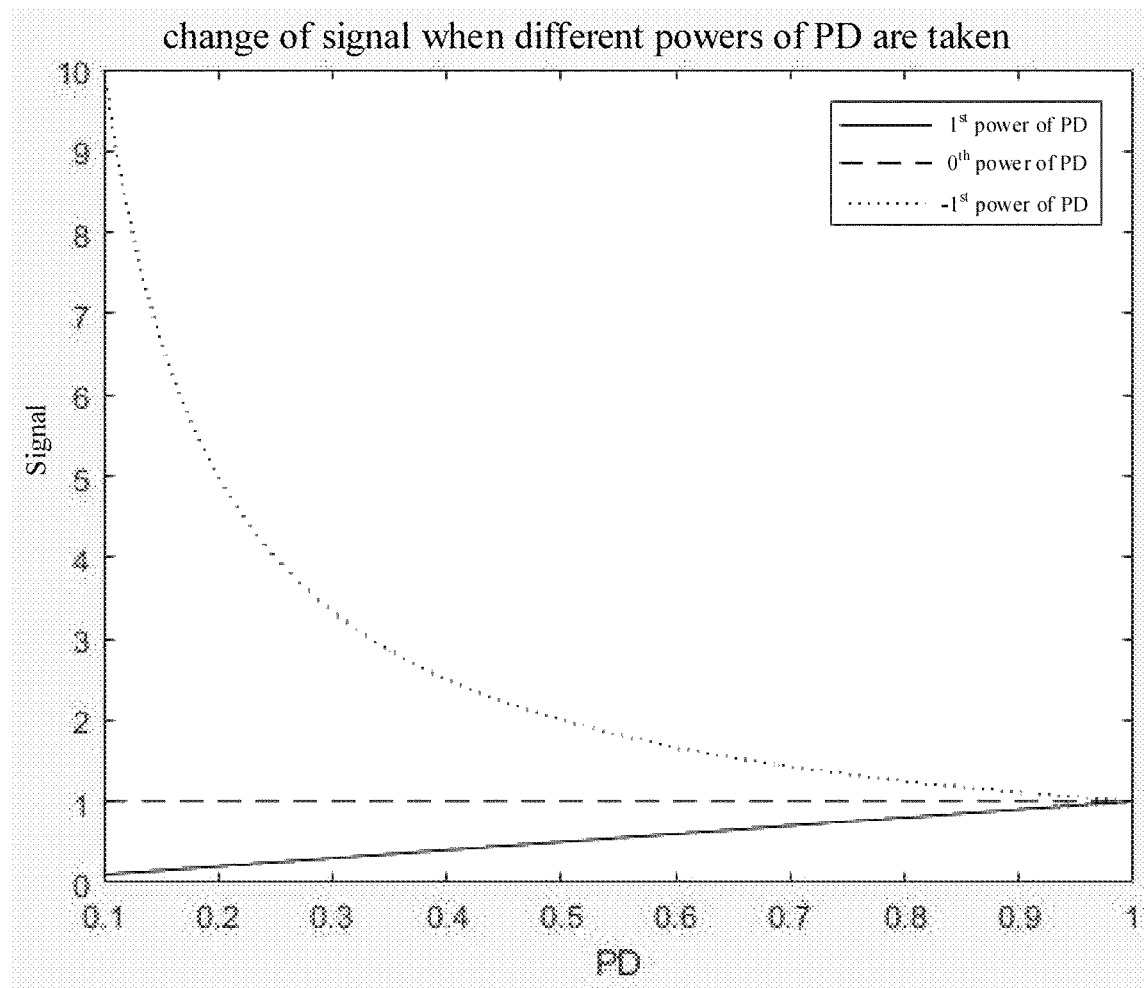
FIG. 5 is a simulation of change of signals when the $1^{st}$ power, the $0^{th}$ power and the $-1^{st}$ power of PD are taken respectively.

The larger T1 and T2 are, the larger PD is. TE and TR are set to negative numbers, and tissue signals with large T1 and T2 are low signals. As shown in FIG. 5, when the positive $1^{st}$ power of PD is taken, the signal increases with the increase of PD; when the $0^{th}$ power of PD is taken, the signal does not change with PD; when the $-1^{st}$ power of PD is taken, the signal decreases with the increase of PD. Therefore, after TE and TR are set to negative numbers, the negative power of PD is taken to calculate the synthetic magnetic resonance image. The larger the PD, T1 and T2, the lower the signal, which can further improve the contrast between different tissues, and can also improve the contrast between a normal tissue and a diseased tissue with elevated PD, T1 and T2.

Figure 8:
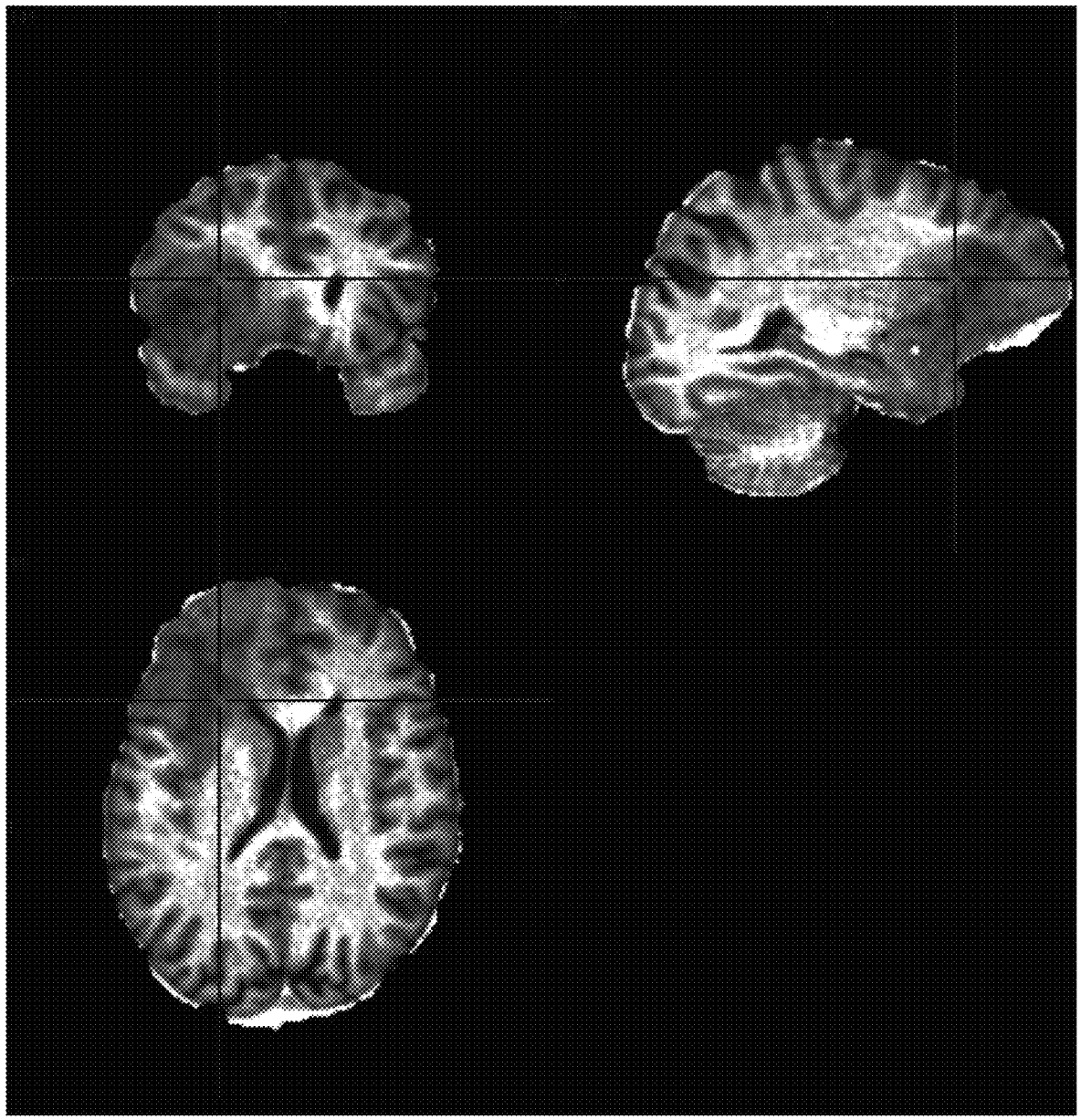
FIG. 8 is a synthetic magnetic resonance image obtained by using PD, T1 and T2 obtained by quantitative magnetic resonance imaging, by using the signal formula of the SE sequence, setting TR to −1200 ms and TE to −5 ms, taking the negative $1^{st}$ power of PD, and taking the absolute value of the signal.

As shown in FIG. 8, by using PD, T1, T2 obtained by quantitative magnetic resonance imaging, using the signal formula of the SE sequence, setting TE as −50 ms, TR as −1200 ms, taking the negative $1^{st}$ power of PD, a synthetic magnetic resonance image is obtained through calculation.

Comparing FIG. 7 with FIG. 8, all conditions are the same, except that FIG. 7 is a synthetic magnetic resonance image obtained by taking the positive $1^{st}$ power of PD, and FIG. 8 is a synthetic magnetic resonance image obtained by taking the negative $1^{st}$ power of PD. By comparing FIG. 7 with FIG. 8, it can be seen that the image contrast of FIG. 8 is greater than that of FIG. 7. Therefore, on the basis of setting TE and TR as negative numbers, taking negative power of PD again can further improve the contrast of the synthetic magnetic resonance image.

Figure 9:
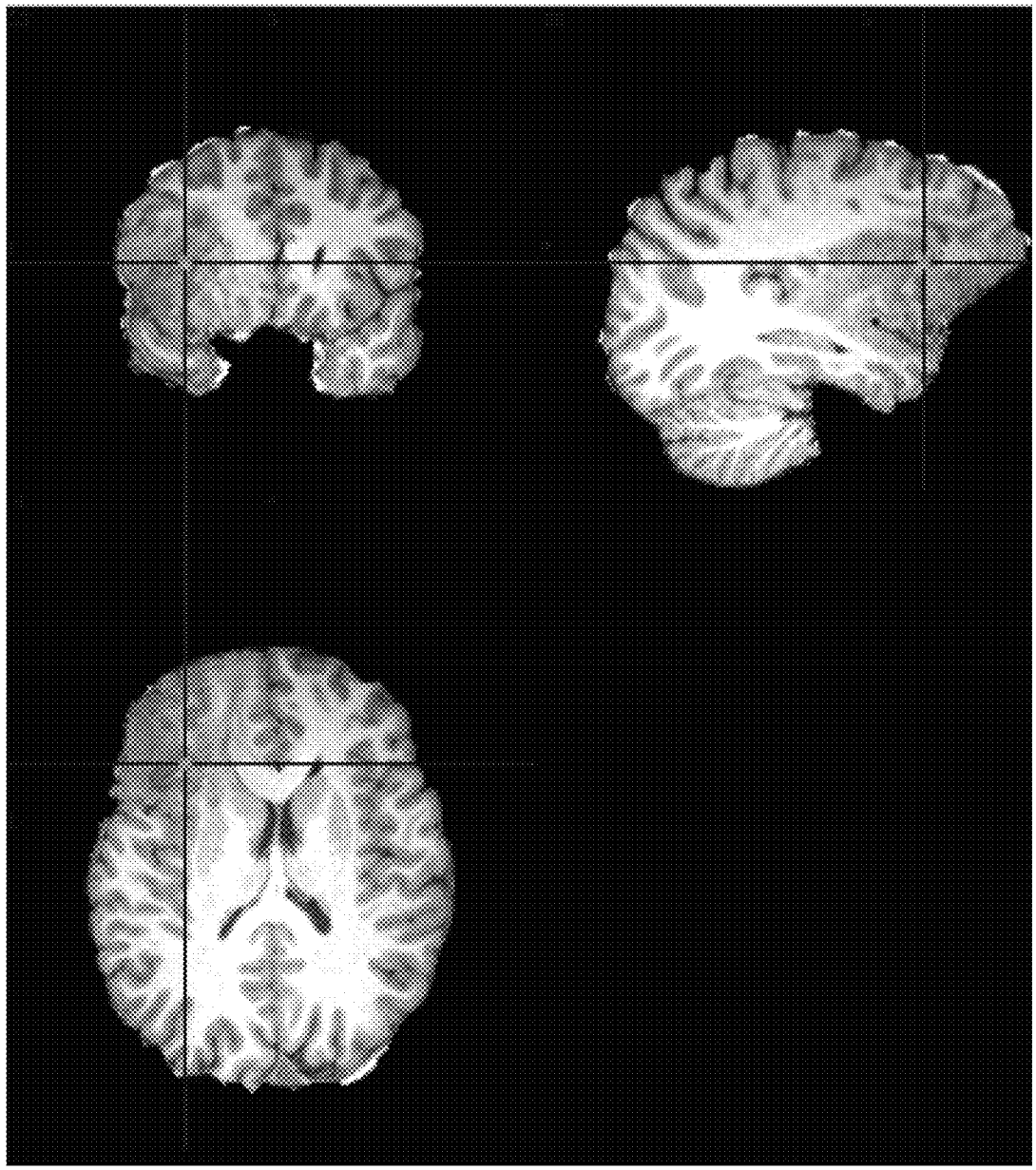
FIG. 9 is a T1-weighted mprage image obtained by conventional clinical scanning.

Comparing FIG. 8 with FIG. 9, FIG. 8 is a synthetic magnetic resonance image obtained by setting TE as −50 ms, TR as −1200 ms, and taking the negative $1^{st}$ power of PD, and FIG. 9 is a T1-weighted mprage image obtained by conventional clinical scanning. By comparing FIG. 8 with FIG. 9, it can be seen that the image contrast of FIG. 8 is higher than that of FIG. 9, and FIG. 8 shows the position and boundary of the lesion more clearly.

The above is only the preferred embodiment of this application. This application is not limited to the specific embodiments described herein, but rather can cover the widest scope consistent with the principles and novel features disclosed herein.

What is claimed is:

1. A method for synthesizing high-quality magnetic resonance images, comprising steps of:
   (1) scanning a subject by a magnetic resonance scanner, and obtaining proton density PD, longitudinal relaxation time T1 and transverse relaxation time T2 by further reconstruction; and
   (2) by image processor substituting PD, T1 and T2 obtained in the step (1) into formula (1) to obtain a magnetic resonance signal S:

$$S \propto PD^{\beta}(1-e^{-TR/T1})e^{-TE/T2} \qquad (1)$$

where β is −1; TR represents simulated repetition time and is negative; and TE represents simulated echo time and is negative, and by image processor generating magnetic resonance images with improve contrast.

\* \* \* \* \*